(12) United States Patent
Khamar et al.

(10) Patent No.: US 8,563,517 B2
(45) Date of Patent: Oct. 22, 2013

(54) DIPEPTIDYL PEPTIDASE IV (DP-IV) COMPOUNDS

(75) Inventors: Bakulesh Mafatlal Khamar, Ahmedabad (IN); Singh Chandan, Ahmedabad (IN); Rajiv Indravadan Modi, Ahmedabad (IN)

(73) Assignee: Cadila Pharmaceuticals Limited, Ahmedabad (IN)

( * ) Notice: Subject to any disclaimer, the term of this patent is extended or adjusted under 35 U.S.C. 154(b) by 52 days.

(21) Appl. No.: 13/063,691

(22) PCT Filed: Sep. 11, 2009

(86) PCT No.: PCT/IB2009/006807
§ 371 (c)(1),
(2), (4) Date: Apr. 8, 2011

(87) PCT Pub. No.: WO2010/029422
PCT Pub. Date: Mar. 18, 2010

(65) Prior Publication Data
US 2011/0183919 A1   Jul. 28, 2011

(30) Foreign Application Priority Data
Sep. 12, 2008   (IN) .......................... 1934/MUM/2008

(51) Int. Cl.
*A61K 38/48* (2006.01)
*A61K 38/55* (2006.01)
*C07K 14/81* (2006.01)

(52) U.S. Cl.
USPC ........................................................ 514/20.1

(58) Field of Classification Search
None
See application file for complete search history.

(56) References Cited

U.S. PATENT DOCUMENTS 7,326,708 B2   2/2008   Cypes et al.
2006/0084604 A1 *   4/2006   Kitaura et al. .................. 514/12

FOREIGN PATENT DOCUMENTS

WO        9515309        6/1995
WO   WO 2004085661 A2 *  10/2004

OTHER PUBLICATIONS

Carlos Garci'a-Aparicio et al., J. Med. Chem. 2006, 49, 5339-5351.*
Wender et al., PNAS, Nov. 21, 2000, vol. 97, No. 24, 13003-13008.*

Rosenblum J.S. et al., "Prolyl peptidases: a serine protease subfamily with high potential for drug discovery," Curr Opin Chem Biol. 2003 Aug; 7(4): 496-504, La Jolla, U.S.A.
Mentlein R. et al., "Dipeptidyl-peptidase IV hydrolyses gastric inhibitory polypeptide, glucagon-like peptide-1(7-36)amide, peptide histidine methionine and is responsible for their degradation in human serum," Eur J Biochem. Jun. 15, 1993; 214(3): 829-35, Germany.
Kieffer T. J. et al., "Degradation of glucose-dependent insulinotropic polypeptide and truncated glucagon-like peptide 1 in vitro and in vivo by dipeptidyl peptidase IV," Endocrinology, Aug. 1995; 136(8): 3585-96.
Kondo T. et al., "Discovery of long-acting N-(cyanomethyl)-N-alkyl-L-prolinamide inhibitors of dipeptidyl peptidase IV," Bioorg Med Chem. Jan. 1, 2008; 16(1): 190-208, Osaka, Japan.
Sakashita H. et al., "1-((S)-gamma-substituted prolyl)-(S)-2-cyanopyrrolidine as a novel series of highly potent DPP-IV inhibitors," Bioorg Med Chem Lett. May 16, 2005; 15(10): 2441-5, Yokohama, Japan.
Tsai Ty et al., "Substituted pyrrolidine-2,4-dicarboxylic acid amides as potent dipeptidyl peptidase IV inhibitors," Bioorg Med Chem Lett. Jun. 15, 2006; 16(12): 3268-72, Taiwan.
Heins J. et al, "Mechanism of proline-specific proteinases: (I) Substrate specificity of dipeptidyl peptidase IV from pig kidney and proline-specific endopeptidase from Flavobacterium meningosepticum," Biochim Biophys Acta. May 18, 1988; 954(2): 161-9.

* cited by examiner

*Primary Examiner* — Marcela M Cordero Garcia
*Assistant Examiner* — Kaipeen Yang
(74) *Attorney, Agent, or Firm* — Pepper Hamilton LLP (57) ABSTRACT

The present invention is directed to novel compounds of formula I and pharmaceutically acceptable salts, enantiomers thereof having inhibiting properties of dipeptidyl peptidase IV enzyme (DP-IV inhibitors). The invention is also directed to pharmaceutical compositions comprising these compounds and the use of these compounds along with its composition in the prevention or treatment of diseases associated with DP-IV enzyme.

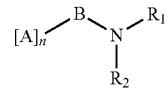

Formula I wherein,
A is defined as $R_3$-$R_4$ wherein $R_3$ and $R_4$ are together or independently defined as peptides having amino acids ranging from 1 to 10,
B is chemical bond between peptide and substituted amine,
$R_1$, and $R_2$ are as defined in specification.

4 Claims, 2 Drawing Sheets

Fig. 01: Kinetic release of compound of interest from compound of formula 5

Fig. 02: Kinetic release of compound of interest from compound of formula 8

Fig. 03: Kinetic release of compound of interest from compound of formula 13

Fig. 04: Kinetic release of compound of interest from compound of formula 15

DIPEPTIDYL PEPTIDASE IV (DP-IV) COMPOUNDS

CROSS-REFERENCE TO RELATED APPLICATIONS

This application is the U.S. National Stage filing of International Application Serial No. PCT/IB2009/006807 filed Sep. 11, 2009, which claims priority to Indian Application No. 1934/MUM/2008 filed Sep. 12, 2008 each of which is incorporated herein by reference in its entirety.

FIELD OF INVENTION

The invention relates to novel anti-diabetic compounds of formula I and includes their stereo isomers and composition containing compound of formula I as pharmaceutically active ingredient and process for preparation thereof.

Formula I wherein,
  A is peptide
  B is peptide bond between peptide and substituted amine.
  $R_1$, and $R_2$ are as defined in specification,

BACKGROUND OF INVENTION

Various amino peptidases are present in the mammals and catalyze the sequential release of peptidase from peptides such as, pyroglutamyl aminopeptidase and prolylaminpeptidase in addition to dipeptidyl peptidase. Dipeptidyl peptidase family includes DP II, DP-IV, DP VIII, DP IX. (*Curr. Opin. Chem. Biol.* 2003, 7, 496) The newly synthesized compounds provide DP-IV inhibition activity sufficiently fast and target rate. The enzyme DP-IV is a part of the CD26 surface region associated with immune regulation, signal transduction and apoptosis. DP-IV enzyme works as a suppressor in the development of cancer and tumours. DP-IV also plays major role in glucose metabolism and responsible for the degradation of incretins such as Glucagon-like peptide-1 (GLP-1). GLP-1 is an incretin hormon secreted by intestinal L-cells in response to food intake. The active form of GLP-1 is having 30-aminoacid peptide, which stimulates insulin, release, inhibits glucagons release, and slows gastric emptying, each a benefit in control of glucose homeostasis in patients with type II diabetes. The activation of GLP-1 is rapidly inactivated by the plasma DP-IV which cleaves a dipeptide from a N-terminal. (*Eur. J. Biochem.*, 1993, 214, 829 and *Endocrinology* 1995, 136, 3585). DP-IV inhibitors offers several potential advantages over existing therapies including decreased risk of hypoglycemia, potential weight loss, and the potential for regeneration and differentiation of pancreatic β-cells. DP-IV also binds to the enzyme adenosine deaminase specifically and with high affinity.

Casomorphin is a particular type of peptide which is protein fragment. Casomorphin can be derived from the digestion of casein proteins in milk and milk products. The most important casomorphins from bovine milk are those released from the digestion of β-casomorphins, sometimes denoted as BCM followed by numeral indicating the number of amino acids in the sequence. The potential release of β-casomorphins varies between species and breeds. Casomorphin is a series of peptides ranging from 3 to 8 amino acids. In present invention, we explore the synthesis of peptide derivatives based on amino acid sequencing of Casomorphin peptides. The different peptides derivatives ranging from 2 to 20 amino acids are synthesized using substituted amine derivatives.

Several DP-IV inhibitors possessing modified proline structure as P2 moiety have been reported as illustrated below. (Bioorg. Med. Chem. Lett. 2008, 16, 190)

In 2005, Sakashita et al., disclosed that (4-substituted)-L-prolyl-(2S)-2-cyanopyrrolidine showed increased inhibition of DP-IV activity relative to unsaturated analogs and that (4β-substituted)-L-prolyl-(2S)-2-cyanopyrrolidine showed 20-fold stronger activity than the corresponding 4α isomer. (*Bioorg. Med. Chem. Lett.* 2005, 15, 2441)

Tsai et al. disclosed that (4βcarbamoyl)-L-prolyl-(2S)-2-cyanopyrrolidine showed enhanced DP-IV inhibition activity, while (5,5-gem-dimethyl)-L-prolyl-(2S)-2-cyanopyrrlidine showed as 500 fold decrease of DP-IV inhibition relative to the unsubstituted analog. (*Bioorg. Med. Chem. Lett.* 2006, 16, 3268)

Heins, J. et al discloses that DP-IV is a serine protease that catalyzes the cleavage of dipeptides from the N-terminus of proteins with the sequence H-X-Pro-Y or H-X-Ala-Y (where X,Y=any amino acid, Y≠Pro.) (*Biochim. Biophys. Acta.,* 1988, 954, 161)

SUMMARY OF INVENTION

The objective of the invention is to provide novel compounds of formula I and pharmaceutically acceptable salts, enantiomers thereof having inhibiting properties of dipeptidyl peptidase IV enzyme (DP-IV inhibitors) sufficiently fast and target rate.

The invention is also provides to pharmaceutical compositions comprising these compounds and the use of these compounds along with its composition in the prevention or treatment of diseases associated with DP-IV enzyme.

Formula I wherein,
  A is peptide
  B is peptide bond between peptide and substituted amine.
  $R_1$, and $R_2$ are as defined in specification,

BRIEF DESCRIPTION OF THE DRAWINGS

FIG. 01: Kinetic release by DPP IV enzyme of a compound of interest from a compound of formula 5
FIG. 02: Kinetic release by DPP IV enzyme of a compound of interest from a compound of formula 8
FIG. 03: Kinetic release by DPP IV enzyme of a compound of interest from a compound of formula 13
FIG. 04: Kinetic release by DPP IV enzyme of a compound of interest from a compound of formula 15

DESCRIPTION OF INVENTION

The newly synthesized peptide derivatives can be used in the treatment of various disorders, especially metabolic disorder associated with diabetes mellitus.

We disclose herein a series of novel compounds that are potential proteases inhibitors. The invention relates to novel peptide derivatives of the formula I, Formula I wherein,

A is peptide;

A is further defined as $R_3$-$R_4$ wherein $R_3$ and $R_4$ are together or independently defined as peptides having amino acids ranging from 1 to 10. The amino acids for the formation of peptides are selected from naturally occurring or synthetic amino acid analogues. The preferred peptides are formed using amino acids selected from glycine, alanine, valine, leucine, isoleucine, phenylalanine, methionine, tryptophan, lysine, glutamine, glutamic acid, serine, proline, cysteine, tyrosine, histidine, arginine, asparagines, aspartic acid, threonine or mixtures of amino acid thereof

B is peptide bond between peptide and substituted amine.

$R_1$ and/or $R_2$ is independently selected from unsubstituted or substituted alkyl; unsubstituted or substituted cycloalkyl; unsubstituted or substituted cycloalkylalkoxy; unsubstituted or substituted $C_{1-6}$ alkylalkoxy; unsubstituted or substituted cycloalkoxy-alkyl; $C_{1-6}$ alkoxy-$C_{1-6}$ alkyl; unsubstituted or substituted phenyl; unsubstituted or substituted benzyl; halogenated $C_{1-6}$ alkyl; $C_{1-6}$alkoxy-$C_{1-6}$alkyl; cycloalkoxy-$C_{1-6}$ alkyl; unsubstituted or substituted aryl; unsubstituted or substituted bicyclo $C_4$-$C_{15}$ compound; heterocycle which may be saturated or unsaturated comprising 1-4 heteroatoms independently selected from N, S and O; the heterocycle being unsubstituted or substituted with 1-3 substituents independently selected from oxo; OH; halogen; $C_{1-6}$ alkyl; and $OC_{1-6}$ alkyl, wherein the $C_{1-6}$ alkyl and $OC_{1-6}$ alkyl are linear or branched and optionally substituted with 1-5 halogens or

$R_1$ and $R_2$ together or independently defined as hydrogen or, -continued -continued

- - - - - indicates the presence of N atom in peptide bonding of formula I.

n is anything in between 0 to 10

$R_5$, $R_6$, $R_7$, or Ar are any of H or $C_{1-4}$ alkyl, —$CH_2CF_3$, —$CH_2CH.dbd.CH_2$, —$CH_2$—$CON(CH_3)_2$, -Ph, —$CH_2$-Ph, —$CH_2$-(4-MeO-Ph), —$CH_2$-(4-Me-Ph), —$CH_2$-(4-CN-Ph), —$CH_2$-(2-CF3Ph), —$CH_2$-(2-F-Ph), —$CH_2$-(4-F-Ph), —$CH(OH)$-(4-F-Ph), —$CH_2$-(3,5-bisCF$_3$-Ph), —$CH_2$-(2-pyridyl), -2,4-dichloro-Ph, -(4-MeO-Ph), -(4-Me-Ph), -(4-CN-Ph), -(2-Me-Ph), -(2-Chloro-Ph), -(2-chloro-4-MeO-Ph), -(2-chloro-4-CN-Ph), -Naphthayl, -(2-F-Ph), -(2,4-di-F-Ph), (2,4,5-tri-F-Ph), a, or b, or c is independently selected from N, S, O, C, and pharmaceutically acceptable salts, enantiomers thereof, to process for the preparation of compounds accordingly to the invention, to pharmaceutical composition containing them and to their use as medicinal active ingredients.

As used herein the following definitions are applicable.

"Alkyl" well as other groups having the prefix "Alk", such as alkoxy and alkanoyl, means carbon chains which may be linear or branched, and combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like. When no number of carbon atoms is specified, $C_{1-6}$ is intended.

"Cycloalkyl" well as other groups having the prefix "alk", such as alkoxy and alkanoyl, means the specified number of carbon atoms permits, e.g., from $C_{3-10}$. "Cycloalkyl" is a subset of alkyl and means a saturated carbocyclic ring having a specified number of carbon atoms. Examples of cycloalkyl include cyclopropyl, cyclobutyl, cyclopentyl, cyclohexyl, cycloheptyl, cyclooctyl, and the like. A cycloalkyl group generally is monocyclic unless stated otherwise. Cycloalkyl groups are saturated unless otherwise defined. are not limited to combinations of linear or branched alkyl chains combined along with cycloalkyl structures.

The term "alkoxy" refers to straight or branched chain alkoxides of the number of carbon atoms specified (e.g., $C_{1-10}$ alkoxy), or any number within this range [i.e., methoxy (MeO—), ethoxy, isopropoxy, etc.].

The term "alkylthio" refers to straight or branched chain alkylsulfides of the number of carbon atoms specified (e.g., $C_{1-10}$ alkylthio), or any number within this range [i.e., methylthio (MeS—), ethylthio, isopropylthio, etc.].

The term "alkylamino" refers to straight or branched alkylamines of the number of carbon atoms specified (e.g., $C_{1-6}$ alkylamino), or any number within this range [i.e., methylamino, ethylamino, isopropylamino, t-butylamino, etc.].

The term "alkylsulfonyl" refers to straight or branched chain alkylsulfones of the number of carbon atoms specified (e.g., $C_{1-6}$ alkylsulfonyl), or any number within this range [i.e., methylsulfonyl (MeSO$_2$—), ethylsulfonyl, isopropylsulfonyl, etc.].

The term "alkyloxycarbonyl" refers to straight or branched chain esters of a carboxylic acid derivative of the present invention of the number of carbon atoms specified (e.g., $C_{1-6}$ alkyloxycarbonyl), or any number within this range [i.e., methyloxycarbonyl (MeOCO—), ethyloxycarbonyl, or butyloxycarbonyl].

"Halogen" or "Halo" refers to fluorine, chlorine, bromine and iodine. Chlorine and fluorine are generally preferred. Fluorine is most preferred when the halogens are substituted on an alkyl or alkoxy group (e.g. $CF_3O$ and $CF_3CH_2O$).

"Aryl" means a mono- or polycyclic aromatic ring system containing carbon ring atoms. The preferred aryls are monocyclic or bicyclic 6-10 membered aromatic ring systems.

"Heterocycle" and "heterocyclyl" refer to saturated or unsaturated non-aromatic rings or ring systems containing at least one heteroatom selected from O, S and N, further including the oxidized forms of sulfur, namely SO and $SO_2$. Examples of heterocycles include tetrahydrofuran (THF), dihydrofuran, 1,4-dioxane, morpholine, 1,4-dithiane, piperazine, piperidine, 1,3-dioxolane, imidazolidine, imidazoline, pyrroline, pyrrolidine, tetrahydropyran, dihydropyran, oxathiolane, dithiolane, 1,3-dioxane, 1,3-dithiane, oxathiane, thiomorpholine, and the like.

"Heteroaryl" means an aromatic or partially aromatic heterocycle that contains at least one ring heteroatom selected from O, S and N. Heteroaryls also include heteroaryls fused to other kinds of rings, such as aryls, cycloalkyls and heterocycles that are not aromatic. Examples of heteroaryl groups include pyrrolyl, isoxazolyl, isothiazolyl, pyrazolyl, pyridinyl, 2-oxo-(1H)-pyridinyl (2-hydroxy-pyridinyl), oxazolyl, 1,2,4-oxadiazolyl, 1,3,4-oxadiazolyl, thiadiazolyl, thiazolyl, imidazolyl, triazolyl, tetrazolyl, furyl, triazinyl, thienyl, pyrimidinyl, pyrazinyl, benzisoxazolyl, benzoxazolyl, benzothiazolyl, benzothiadiazolyl, dihydrobenzofuranyl, indolinyl, pyridazinyl, indazolyl, isoindolyl, dihydrobenzothienyl, indolizinyl, cinnolinyl, phthalazinyl, quinazolinyl, naphthyridinyl, carbazolyl, benzodioxolyl, quinoxalinyl, purinyl, furazanyl, isobenzylfuranyl, benzimidazolyl, benzofuranyl, benzothienyl, quinolyl, indolyl, isoquinolyl, dibenzofuranyl, imidazo[1,2-a]pyridinyl, [1,2,4-triazolo][4,3-a]pyridinyl, pyrazolo[1,5-a]pyridinyl, [1,2,4-triazolo][1,5-a]pyridinyl, 2-oxo-1,3-benzoxazolyl, 4-oxo-3H-quinazolinyl, 3-oxo-[1,2,4]-triazolo[4,3-a]-2H-pyridinyl, 5-oxo-[1,2,4]-4H-oxadiazolyl, 2-oxo-[1,3,4]-3H-oxadiazolyl, 2-oxo-1,3-dihydro-2H-imidazolyl, 3-oxo-2,4-dihydro-3H-1,2,4-triazolyl, and the like. For heterocyclyl and heteroaryl groups, rings and ring systems containing from 3-15 atoms are included, forming 1-3 rings.

All Aryl and heteroaryl in aryl-$C_{1-6}$alkoxy, aryl-$C_{1-6}$alkyl and the like is for example, phenyl, naphthyl that is unsubstituted or mono, di- or tri-substituted by linear or branched or its unsubstituted or substituted 1-5 halogenated-alkyl, halogen, trifluoromethyl, trifluoromethyloxy, pentafluoromethyl, pentafluoromethyloxy and/or trifluoroethyl, Bicyclo compound is for example $C_4$ to $C_{25}$ member, preferably 5-, 6-, 7-, 8-, 9-, 10-member bicycle compounds which is unsubstituted or substituted with heterocycle or may include any of the possible functions groups. The possible substitution in compound of formula I or its analogues contain any of the hydrogen, OH, carboxy, halogen, amino, amido, cyano, ester, acid chloride, carboxylic acid, aldehyde, ether, anhydride, acetyl, acetoxy, substituted phenyl, substituted benzyl.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, N,N'-dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, fumaric, tartaric acids and the like.

It will be understood that, as used herein, references to the compounds of formula I are meant to also include the pharmaceutically acceptable salts.

As appreciated by those of skill in the art, halo or halogen as used herein are intended to include fluoro, chloro, bromo and iodo. Similarly, $C_{1-8}$, as in $C_{1-8}$ alkyl is defined to identify the group as having 1, 2, 3, 4, 5, 6, 7 or 8 carbons in a linear or branched arrangement, such that $C_{1-8}$ alkyl specifically includes methyl, ethyl, n-propyl, iso-propyl, n-butyl, iso-butyl, tert-butyl, pentyl, hexyl, heptyl and octyl. Likewise, $C_0$, as in $C_0$ alkyl is defined to identify the presence of a direct covalent bond. A group which is designated as being independently substituted with substituents may be independently substituted with multiple numbers of such substituents.

The compounds of the present invention may contain one or more asymmetric centres and can thus occur as racemates and racemic mixture, single enantiomers, diastereomeric mixtures and individual diastereomers. The compounds of the instant invention have one asymmetric centre at beta carbon atom. Additional asymmetric centres may be present depending upon the nature of the various substituents on the molecule. Each such asymmetric center will independently produce two optical isomers and it is intended that all of the possible optical isomers and diastereomers in mixtures and as pure or partially purified compound are included within the ambit of this invention. The present invention is meant to comprehend all such isomeric forms of these compounds.

The compound described herein can contain olefinic double bonds, and unless specific otherwise, are meant to include both E and Z geometric isomers.

The compound described herein can exist as tutomers. The individual tautomers as well as mixtures thereof are encompassed with compounds of the present invention.

Formula I shows the structure of the class of compounds without preferred stereochemistry. The preferred stereochemistry at the carbon atom which is attached to and $R_9$ of the beta amino acid from which these compounds are prepared.

The independent syntheses of these peptide derivatives or their chromatographic separations may be achieved as known in the art by appropriate modification of the methodology disclosed herein. Their absolute stereochemistry can be determined by the x-ray crystallography of crystalline products or crystalline intermediates which are derivatized, if necessary, with a reagent containing an asymmetric center of known absolute configuration.

If desired, racemic mixtures of the compounds may preferably separate so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The terms "administration of" and/or "administering a" compound should be understood to mean providing a compound of the invention or a prodrug of a compound of the invention to the individual in need of treatment.

The general synthetic route for the preparation of compound having formula 1 involves following general scheme wherein the scheme is exemplified with the selected amino acids as proline with different amino acid to form peptides. The peptide compounds synthesized herein using different amino acid consist peptide bond. The intermediate peptide compound further reacts with different primary and secondary amine derivative to give compound of the formula I.

Aa = Different amino acids
Pro = Proline
n = 0 to 10

The process disclosed herein is not limited to the preparation of specific compounds as prepared herein but is described the general state of art in order to prepare the compounds of present invention. It also includes a compound which selected from the group consisting of the compounds disclosed in the following examples and pharmaceutically acceptable salts thereof and individual diastereomers thereof.

Example-1

Preparation of 1-(2-Amino-3-methyl-butyryl)-pyrrolidine-2-carboxylic acid [3-oxo-1-(2,4,5-trifluorobenzyl)-3-(3-trifluoromethyl-5,6-dihydro-8H-[1,2,4] triazolo[4,3-a]pyrazin-7-yl)-propyl]-amide Hydrochloride STEP-1: Preparation 1-(2-tert-Butoxycarbonylamino-3-methyl-butyryl)-pyrrolidine-2-carboxylic acid 2-tert-Butoxycarbonylamino-3-methyl-butyric acid
Formula 2

1-(2-tert-Butoxycarbonylamino-3-methyl-
butyryl)-pyrrolidine-2-carboxylic acid
Formula 3

To a stirred solution of N-Boc L-Valine (Compound of formula 2) [8 gm, 0.037 mole] and tri ethyl amine (5.15 ml, 0.037 mole) in THF (120 ml), ethyl chloro formate (3.52 ml, 0.037 mole) was added dropwise at 0-5° C. The reaction was stirred at 0° C. for 15 minutes and stirred at room temperature for 1 hour. Then keep the reaction at 0° C. and add mixture of tri ethyl amine (10.3 ml, 0.074 mole) and THF (60 ml).

Finally L-Proline (4.25 gm, 0.037 mole) was added to above mixture at 0° C. Reaction was stirred at 0° C. for 30 minutes and stirred at room temperature for over night. After being stirred, THF was concentrated under vacuum and residue was acidified with 1N HCl (till pH~3). The product layer was extracted with ethyl acetate. The organic extracts were dried over Na$_2$SO$_4$ and concentrated to give (B). The resulted product was subjected to column chromatography using EtoAC/Hexane 5/5 as an eluent to give N-Boc Val-Pro (Compound of formula 3). (Yield=3.6 gm, 31%)

STEP-2: Preparation of (2-Methyl-1-{2-[3-oxo-1-(2,4,5-trifluoro-benzyl)-3-(3-trifluoromethyl-5,6-dihydro-8H-[1,2,4]triazolo[4,3-a]pyrazin-7-yl)-propyl-carbamoyl]-pyrrolidine-1-carbonyl}-propyl)-carbamic acid tert-butyl ester (Compound of Formula 4)

1-(2-tert-Butoxycarbonylamino-3-methyl-
butyryl)-pyrrolidine-2-carboxylic acid
Formula 3

3-Amino-1-(3-trifluoromethyl-5,6,7,8-
tetrahydro-[1,2,4]triazolo[4,3-a]pyridin-7-yl)-
4-(2,4,5-trifluoro-phenyl)-butan-1-one

DCC, MDC | 0° C.

Formula 4
(2-Methyl-1-{2-[3-oxo-1-(2,4,5-trifluoro-benzyl)-3-(3-trifluoromethyl-5,6,7,8-
tetrahydro-[1,2,4]triazolo[4,3-a]pyridin-7-yl)-propylcarbamoyl]-pyrrolidine-1-
carbonyl}-propyl)-carbamic acid tert-butyl ester

To a stirred solution of N-BoC Val-Pro (Compound of formula 3) (0.39 gm, 1.23 mmol) in MDC (40 ml), dicyclohexyl di-carbobiimide (0.4 gm, 0.0019 mole) was added at 0° C., the reaction mixture was stirred for 5-10 minutes at 0° C. Then 3-Amino-1-(3-trifluoromethyl-5,6,7,8-tetrahydro-[1,2,4]triazolo[4,3-a]pyridin-7-yl)-4-(2,4,5-trifluoro-phenyl)-butan-1-one (0.5 gm, 0.00123 mole) was added to this mixture at 0° C. Then reaction was stirred at room temperature for 4 hours. Take the TLC for the completion of reaction.

Reaction mixture was filtered to remove urea derivative of DCC. Then filtrate was concentrated in vacuum. Take the column chromatography of this compound for purification using CHCl$_3$/MeOH (9/1) as a solvent system to give (2-Methyl-1-{2-[3-oxo-1-(2,4,5-trifluoro-benzyl)-3-(3-trifluoromethyl-5,6-dihydro-8H-[1,2,4]triazolo[4,3-a]pyrazin-7-yl)-propylcarbamoyl]-pyrrolidine-1-carbonyl}-propyl)-carbamic acid tert-butyl ester (Compound of formula 4) [0.54 gm, 62% yield].

STEP-3: Preparation of 1-(2-Amino-3-methyl-butyryl)-pyrrolidine-2-carboxylic acid [3-oxo-1-(2,4,5-trifluoro-benzyl)-3-(3-trifluoromethyl-5,6-dihydro-8H-[1,2,4]triazolo[4,3-a]pyridin-7-yl)-propyl]-amide Hydrochloride (Compound of Formula 5)

Formula 4
(2-Methyl-1-{2-[3-oxo-1-(2,4,5-trifluoro-benzyl)-3-(3-trifluoromethyl-5,6,7,8-tetrahydro-[1,2,4]triazolo[4,3-a]pyridin-7-yl)-propylcarbamoyl]-pyrrolidine-1-carbonyl}-propyl)-carbamic acid tert-butyl ester Formula 5
1-(2-Amino-3-methyl-butyryl)-pyrrolidine-2-carboxylic acid [3-oxo-1-(2,4,5-trifluoro-benzyl)-3-(3-trifluoromethyl-5,6,7,8-tetrahydro-[1,2,4]triazolo[4,3-a]pyridin-7-yl)-propyl]-amide

To a stirred solution of (2-Methyl-1-{2-[3-oxo-1-(2,4,5-trifluoro-benzyl)-3-(3-trifluoromethyl-5,6-dihydro-8H-[1,2,4]triazolo[4,3-a]pyrazin-7-yl)-propylcarbamoyl]-pyrrolidine-1-carbonyl}-propyl)-carbamic acid tert-butyl ester (Compound of formula 4) (0.54 gm, 0.00077 mole) in ethyl acetate (5 ml), solution of 3M HCl in ethyl acetate (5 ml) was added at room temperature. Then reaction was stirred at room temperature for 1 hour. Take the TLC for the completion of reaction.

Then finally, reaction mixture was concentrated in vacuum to give Hydrochloride salt of 1-(2-Amino-3-methyl-butyryl)-pyrrolidine-2-carboxylic acid [3-oxo-1-(2,4,5-trifluoro-benzyl)-3-(3-trifluoromethyl-5,6-dihydro-8H-[1,2,4]triazolo[4,3-a]pyrazin-7-yl)-propyl]-amide. Thus obtain hydrochloric acid salt of compound is treated with sodium bicarbonate to give (Compound of formula 5). [0.46 gm, 93.88% yield]

Example-2

{1-[3-oxo-1-(2,4,5-trifluoro-benzyl)-3-(3-trifluoromethyl-5,6-dihydro-8H-[1,2,4]triazolo[4,3-a]pyrazin-7-yl)-propylcarbamoyl]-ethyl}-carbamic acid tert-butyl ester (Compound of Formula 6)

STEP-1: Preparation of {1-[3-Oxo-1-(2,4,5-trifluoro-benzyl)-3-(3-trifluoromethyl-5,6-dihydro-8H-[1,2,4]triazolo[4,3-a]pyrazin-7-yl)-propylcarbamoyl]-ethyl}-carbamic acid tert-butyl ester (Compound of Formula 6)

2-tert-Butoxycarbonyl amino-propionic acid

3-Amino-1-(3-trifluoromethyl-5,6,7,8-tetrahydro-[1,2,4]triazolo[4,3-a]pyridin-7-yl)-4-(2,4,5-trifluoro-phenyl)-butan-1-one

DCC, CH₂Cl₂

Formula 6
{1-[3-Oxo-1-(2,4,5-trifluoro-benzyl)-3-(3-trifluoromethyl-5,6-dihydro-8H-[1,2,4]triazolo[4,3-a]pyrazin-7-yl)-propylcarbamoyl]-ethyl}-carbamic acid tert-butyl ester

To a stirred solution of N-BoC-Alanine (1 gm, 0.00245 mole) in $CH_2Cl_2$ (30 ml) was added in dicyclohexyl dicarbodiimide (1 gm, 0.00245×1.5 mole) at 0° C. The reaction mixture was stirred for 15 minutes and to this stirred mixture was added 3-Amino-1-(3-trifluoromethyl-5,6,7,8-tetrahydro-[1,2,4]triazolo[4,3-a]pyridin-7-yl)-4-(2,4,5-trifluoro-phenyl)-butan-1-one (1 gm, 0.00245 mole) at 0° C. The reaction mixture was then stirred for 4 hours at room temperature. After being stirred dicyclohexyl urea was removed by filtration and filtrate was concentrated in vacuum. The residue was purified by silica gel chromatography using $CH_2Cl_2$/MeOH (9.7:0.3) as an eluent to yield {1-[3-oxo-1-(2,4,5-trifluoro-benzyl)-3-(3-trifluoromethyl-5,6-dihydro-8H-[1,2,4]triazolo[4,3-a]pyrazin-7-yl)-propylcarbamoyl]-ethyl}-carbamic acid tert-butyl ester (Compound of formula 6). [1.3 gm, 92%]

STEP-2: Preparation of (2-Methyl-1-{1-[3-oxo-1-(2,4,5-trifluoro-benzyl)-3-(3-trifluoromethyl-5,6-dihydro-8H-[1,2,4]triazolo[4,3-a]pyrazin-7-yl)-propylcarbamoyl]-ethylcarbamoyl}-propyl)-carbamic acid tert-butyl ester (Compound of Formula 7)

{1-[3-Oxo-1-(2,4,5-trifluoro-benzyl)-3-(3-trifluoromethyl-5,6-dihydro-8H-[1,2,4]triazolo[4,3-a]pyrazin-7-yl)-propylcarbamoyl]-ethyl}-carbamic acid tert-butyl ester
Formula 6 i) 3M HCl, EtOAC aq. NaHCO₃
ii) DCC, N-Boc, L-Valine $CH_2Cl_2$ (2-Methyl-1-{1-[3-oxo-1-(2,4,5-trifluoro-benzyl)-3-(3-trifluoromethyl-5,6-dihydro-8H-[1,2,4]triazolo[4,3-a]pyrazin-7-yl)-propylcarbamoyl]-ethylcarbamoyl}-propyl)-carbamic acid tert-butyl ester
Formula 7

To a compound, {1-[3-Oxo-1-(2,4,5-trifluoro-benzyl)-3-(3-trifluoromethyl-5,6-dihydro-8H-[1,2,4]triazolo[4,3-a]pyrazin-7-yl)-propylcarbamoyl]-ethyl}-carbamic acid tert-butyl ester (Compound of formula 6) (1 gm, 0.00173 moles) was added 3M HCl-EtoAC (10 ml) at room temperature. The reaction mixture was then stirred for 1 hour at room temperature. After being stirred, EtoAC was removed to get hydrochloride salt of 2-Amino-N-[3-oxo-1-(2,4,5-trifluoro-benzyl)-3-(3-trifluoromethyl-5,6-dihydro-8H-[1,2,4]triazolo[4,3-a]pyrazin-7-yl)-propyl]-propionamide. Thus hydrochloride salt was dissolved in saturated aq. $NaHCO_3$ and was extracted with EtoAC (30 ml×3). The combined EtoAC layers were dried over $Na_2SO_4$ and were concentrated to get (Ala-Sitagliptin, 0.860 gm, 97% yield). Thus, free base was used in further step.

To a stirred solution of 2-tert-Butoxycarbonylamino-3-methyl-butyric acid (0.390 gm, 0.00179 moles) in $CH_2Cl_2$ (40 ml) was added at 0° C. The reaction mixture was then stirred for 15 minutes. To this stirred solution was added 2-Amino-N-[3-oxo-1-(2,4,5-trifluoro-benzyl)-3-(3-trifluoromethyl-5,6-dihydro-8H-[1,2,4]triazolo[4,3-a]pyrazin-7-yl)-propyl]-propionamide (0.860 gm, 0.00179 moles) at 0° C. The reaction mixture was then stirred for overnight. Dicyclohexyl urea was removed by filtration and filtrate was concentrated in vacuum. The residue was purified by silica gel chromatography using $CH_2Cl_2$/MeOH (9.7/0.3) as an eluent to yield (2-Methyl-1-{1-[3-oxo-1-(2,4,5-trifluoro-benzyl)-3-(3-trifluoromethyl-5,6-dihydro-8H-[1,2,4]triazolo[4,3-a]pyrazin-7-yl)-propylcarbamoyl]-ethylcarbamoyl}-propyl)-carbamic acid tert-butyl ester (Compound of formula 7) (Yield=0.7 gm, 58%)

STEP-3: Preparation of 2-Amino-3-methyl-N-{1-[3-oxo-1-(2,4,5-trifluoro-benzyl)-3-(3-trifluoromethyl-5,6-dihydro-8H-[1,2,4]triazolo[4,3-a]pyrazin-7-yl)-propylcarbamoyl]-ethyl}-butyramide Hydrochloride (Compound of Formula 8)

(2-Methyl-1-{1-[3-oxo-1-(2,4,5-trifluoro-benzyl)-3-(3-trifluoromethyl-5,6-dihydro-8H-[1,2,4]triazolo[4,3-a]pyrazin-7-yl)-propylcarbamoyl]-ethylcarbamoyl}-propyl)-carbamic acid tert-butyl ester
Formula 7

2-Amino-3-methyl-N-{1-[3-oxo-1-(2,4,5-trifluoro-benzyl)-3-(3-trifluoromethyl-5,6-dihydro-8H-[1,2,4]triazolo[4,3-a]pyrazin-7-yl)-propylcarbamoyl]-ethyl}-butyramide Hydrochloride
Formula 8

To a compound (2-Methyl-1-{1-[3-oxo-1-(2,4,5-trifluoro-benzyl)-3-(3-trifluoromethyl-5,6-dihydro-8H-[1,2,4]triazolo[4,3-a]pyrazin-7-yl)-propylcarbamoyl]-ethylcarbamoyl}-propyl)-carbamic acid tert-butyl ester (Compound of formula 7), (500 mg, 0.00073 moles) was added in 3M HCl-EtoAC (10 ml) at room temperature. The reaction mixture was then stirred for 1 hour. It was then concentrated to get 2-Amino-3-methyl-N-{1-[3-oxo-1-(2,4,5-trifluoro-benzyl)-3-(3-trifluoromethyl-5,6-dihydro-8H-[1,2,4]triazolo[4,3-a]pyrazin-7-yl)-propylcarbamoyl]-ethyl}-butyramide Hydrochloride (Compound of formula 8) (430 mg, 94% yield).

Example-3

[1-(2-{[1-(2-amino-3-methylbutanoyl)cyclopentyl]
carbonylamino}-3-methyl-bytanoyl)-pyrrolidin-2-
yl]-N-{3-oxo-3-[3-(trifluoromethyl)(1,2,4-triazolo[4,
3-a]piperidin-6-yl)]-1-[(2,4,5-trifluorophenyl)
methyl]propyl}-carboxamide (Compound of
Formula 21)

STEP-1: Preparation of 1-(2-Amino-3-methyl-butyryl)-pyrrolidine-2-carboxylic acid [3-oxo-1-(2,4,5-trifluoro-benzyl)-3-(3-trifluoromethyl-5,6-dihydro-8H-[1,2,4]triazolo[4,3-a]pyrazin-7-yl)-propyl]-amide (Compound of Formula 18)

Formula 9

Formula 10

1-(2-Amino-3-methyl-butyryl)-pyrrolidine-2-carboxylic acid [3-oxo-1-(2,4,5-trifluoro-benzyl)-3-(3-trifluoromethyl-5,6-dihydro-8H-[1,2,4]triazolo[4,3-a]pyrazin-7-yl)-propyl]-amide Hydrochloride (Compound of formula 9) (520 mg, 0.8 mmole) was dissolve in water 95 ml). Then saturated sodium bicarbonate solution (6 ml) was added to this solution till pH become basic (pH~10) for breaking of Hydrochloride salt. Then compound was extracted with EtoAC (3×75 ml). Organic extracts was dried over Na₂SO₄ and concentrated under vacuum to yield 1-(2-Amino-3-methyl-butyryl)-pyrrolidine-2-carboxylic acid [3-oxo-1-(2,4,5-trifluoro-benzyl)-3-(3-trifluoromethyl-5,6-dihydro-8H-[1,2,4]triazolo[4,3-a]pyrazin-7-yl)-propyl]-amide free base (Compound of formula 10). (Yield=480 mg=98%).

STEP-2: Preparation of (tert-butoxy)-N-{1-(methylethyl)-2-[2-(N-{1-(methylethyl)-2-oxo-2-[2-(N-{3-oxo-3-[3-(trifluoromethyl)(1,2,4-triazolo[4,3-a]piperidin-6-yl)]-1-[(2,4,5-trifluorophenyl)methyl]propyl}carbamoyl)pyrrolidinyl]ethyl}carbomyl)cyalopentyl]-2-oxoethyl}carboxamide (Compound of Formula 11)

To a stirred solution of 1-(2-tert-Butoxycarbonylamino-3-methyl-butyryl)-pyrrolidine-2-carboxylic acid (274 mg, 0.87 mmole) in MDC (20 ml), dicyclohexyl dicarboiimide (DCC) (270 mg, 1.3 mmole) was added and stirred at 0° C. for 5-10 minutes. Then 1-(2-Amino-3-methyl-butyryl)-pyrrolidine-2-carboxylic acid [3-oxo-1-(2,4,5-trifluoro-benzyl)-3-(3-trifluoromethyl-5,6-dihydro-8H-[1,2,4]triazolo[4,3-a]pyrazin-7-yl)-propyl]-amide free base (Compound of formula 10) (480 mg, 0.79 mmole) was added to this mixture at 0° C. Then reaction was stirred at room temperature for 4 hour. Take the TLC for the completion of reaction.

Reaction mixture was filtered to remove urea derivative of DCC. Then filtrate was concentrated in vacuum. Take the column chromatography of this compound for purification using CH$_2$Cl$_2$/MeOH (9.5/0.5) as a solvent system to give (tert-butoxy)-N-{1-(methylethyl)-2-[2-(N-{1-(methylethyl)-2-oxo-2-[2-(N-{3-oxo-3-[3-(trifluoromethyl) (1,2,4-triazolo[4,3-a]piperidin-6-yl)]-1-[(2,4,5-trifluorophenyl)methyl]propyl}carbamoyl)pyrrolidinyl]ethyl}carbomyl)cyalopentyl]-2-oxoethyl}carboxamide (Compound of formula 11) (400 mg, 62%).

STEP-3: Preparation of [1-(2-{[1-(2-amino-3-methylbutanoyl)cyclopentyl]carbonylamino}-3-methylbytanoyl)pyrrolidin-2-yl]-N-{3-oxo-3-[3-(trifluoromethyl)(1,2,4-triazolo[4,3-a]piperidin-6-yl)]-1-[(2, 4,5-trifluorophenyl)methyl]propyl}carboxamide Hydrochloride (Compound of Formula 20)

To a stirred solution of (tert-butoxy)-N-{1-(methylethyl)-2-[2-(N-{1-(methylethyl)-2-oxo-2-[2-(N-{3-oxo-3-[3-(trifluoromethyl)(1,2,4-triazolo[4,3-a]piperidin-6-yl)]-1-[(2,4,5-trifluorophenyl)methyl]propyl}carbamoyl)pyrrolidinyl] ethyl}carbomyl)cyalopentyl]-2-oxoethyl}carboxamide (Compound of formula 11) (400 mg, 0.5 mmole) in ethyl acetate (5 ml), the solution of 3M HCl in Ethyl acetate (4 ml) was added at room temperature. Then reaction was stirred at room temperature for 1 hour. Take the TLC for completion of reaction.

Then finally reaction mixture was concentrated in vacuum to give [1-(2-{[1-(2-amino-3-methylbutanoyl)cyclopentyl]carbonylamino}-3-methylbytanoyl)pyrrolidin-2-yl]-N-{3-oxo-3-[3-(trifluoromethyl) (1,2,4-triazolo[4,3-a]piperidin-6-

Formula 11

Formula 12 yl)]-1-[(2,4,5-trifluorophenyl)methyl]propyl}carboxamide Hydrochloride (Compound of formula 12) (0.350 gm, 95% yield).

Step-4: [1-(2-{[1-(2-amino-3-methylbutanoyl)cyclopentyl]carbonylamino}-3-methylbytanoyl)pyrrolidin-2-yl]-N-{3-oxo-3-[3-(trifluoromethyl)(1,2,4-triazolo[4,3-a]piperidin-6-yl)]-1-[(2,4,5-trifluorophenyl)methyl]propyl}carboxamide Hydrochloride (Compound of Formula 12) to [1-(2-{[1-(2-amino-3-methylbutanoyl)cyclopentyl]carbonylamino}-3-methylbytanoyl)pyrrolidin-2-yl]-N-{3-oxo-3-[3-(trifluoromethyl)(1,2,4-triazolo[4,3-a]piperidin-6-yl)]-1-[(2,4,5-trifluorophenyl)methyl]propyl}carboxamide (Compound of Formula 13)

[1-(2-{[1-(2-amino-3-methylbutanoyl)cyclopentyl]carbonylamino}-3-methylbytanoyl)pyrrolidin-2-yl]-N-{3-oxo-3-[3-(trifluoromethyl)(1,2,4-triazolo[4,3-a]piperidin-6-yl)]-1-[(2,4,5-trifluorophenyl)methyl]propyl}carboxamide Hydrochloride (Compound of formula 12) (265 gm, 0.32 mmol) was dissolve in water (5 ml) and then saturated with NaHCO₃. So, the hydrochloride salt was breaking. Then compound was extracted with EtoAC (3×75 ml). Organic extracts was dried over Na2SO4 and concentrated under vaccuo to yield [1-(2-{[1-(2-amino-3-methylbutanoyl)cyclopentyl]carbonylamino}-3-methylbytanoyl)pyrrolidin-2-yl]-N-{3-oxo-3-[3-(trifluoromethyl)(1,2,4-triazolo[4,3-a]piperidin-6-yl)]-1-[(2,4,5-trifluorophenyl)methyl]propyl}carboxamide (Compound of Formula 13) (245 mg, 97%).

Example-4

(tert-butoxy)-N-{1-(methylethyl)-2-[2-(N-{1-(methylethyl)-2-[2-(N-{1-methylethyl)-2-oxo-2-[2-(N-{3-oxo-3-[3-(trifluoromethyl)(1,2,4-triazolo[4,3-a]piperidin-6-yl]-1-[2,4,5-trifluorophenyl)methyl]propyl}carbamoyl)pyrrolidinyl]ethyl}carbamoyl)pyrrolidinyl]-2-oxoethyl}carbamoyl)pyrrolidinyl]-2-oxoethyl}carboxamide (Compound of Formula 22)

STEP-1: Preparation of [1-(2-{[1-(2-amino-3-methylbutanoyl)cyclopentyl]carbonylamino}-3-methylbytanoyl)pyrrolidin-2-yl]-N-{3-oxo-3-[3-(trifluoromethyl) (1,2,4-triazolo[4,3-a]piperidin-6-yl)]-1-[(2,4,5-trifluorophenyl)methyl]propyl}carboxamide (Compound of Formula 21)

[1-(2-{[1-(2-amino-3-methylbutanoyl)cyclopentyl]carbonylamino}-3-methylbytanoyl)pyrrolidin-2-yl]-N-{3-oxo-3-[3-(trifluoromethyl) (1,2,4-triazolo[4,3-a]piperidin-6-yl)]-1-[(2,4,5-trifluorophenyl)methyl]propyl}carboxamide Hydrochloride (Compound of formula 12) (265 gm, 0.32 mmol) was dissolve in water (5 ml) and then saturated with NaHCO₃. So, the hydrochloride salt was breaking. Then compound was extracted with EtoAC (3×75 ml). Organic extracts was dried over Na2SO4 and concentrated under vaccuo to yield [1-(2-{[1-(2-amino-3-methylbutanoyl)cyclopentyl]carbonylamino}-3-methylbytanoyl)pyrrolidin-2-yl]-N-{3-oxo-3-[3-(trifluoromethyl) (1,2,4-triazolo[4,3-a]piperidin-6-yl)]-1-[(2,4,5-trifluorophenyl)methyl]propyl}carboxamide (Compound of formula 13) (245 mg, 97%).

STEP-2: Preparation Of (tert-butoxy)-N-{1-(methylethyl)-2-[2-(N-{1-(methylethyl)-2-[2-(N-{1-methylethyl)-2-oxo-2-[2-(N-{3-oxo-3-[3-(trifluoromethyl)(1,2,4-triazolo[4,3-a]piperidin-6-yl]-1-[2,4,5-trifluorophenyl)methyl]propyl}carbamoyl)pyrrolidinyl]ethyl}carbamoyl)pyrrolidinyl]-2-oxoethyl}carbamoyl)pyrrolidinyl]-2-oxoethyl}carboxamide (Compound of Formula 14)

To the stirred solution of 1-(2-tert-Butoxycarbonylamino-3-methyl-butyryl)-pyrrolidine-2-carboxylic acid (100 mg, 0.3 mmol) in MDC (20 ml) was added dicyclohexyl dicarbodiimide (DCC) (98 mg, 0.47 mmol) at 0° C. The reaction was stirred at 0° C. for 10 minutes. After being stirring [1-(2-{[1-(2-amino-3-methylbutanoyl)cyclopentyl]carbonylamino}-3-methylbytanoyl)pyrrolidin-2-yl]-N-{3-oxo-3-[3-(trifluoromethyl)(1,2,4-triazolo[4,3-a]piperidin-6-yl)]-1-[(2,4,5-trifluorophenyl)methyl]propyl}carboxamide (Compound of formula 13) (254 mg, 0.3 mmol) was added to this reaction mixture at 0° C. Reaction was stirred for 30 minutes at 0° C. and for 4 hours at room temperature. Take the TLC for the completion of reaction.

Formula 13

1-(2-tert-Butoxycarbonylamino-3-methyl-butyryl)-pyrrolidine-2-carboxylic acid

DCC, MDC, 0° C.

Formula 14

Reaction was filtered to remove urea derivative of DCC. Then filtrate was concentrated in vaccuo. Take the column chromatography for the purification. (Compound of formula 14) (180 mg, 51%).

STEP-3: Preparation of hydrochloride salt of [1-(2-amino-3-methylbutanoyl)pyrrolidin-2-yl]-N-{1-(methylethyl)-2-[2-(N-{1-(methylethyl)-2-oxo-2-(N-{3_oxo-3-[3-(trifluoromethyl)(1,2,4-triazolo[4,3-a]piperidin-6-yl)]-1-[(2,4,5-trifluorophenyl)methyl]propyl}carbamoyl)pyrrolidinyl]ethyl}carbamoyl)pyrrolidinyl]-2-oxoethyl}carboxamide Hydrochloride (Compound of Formula 23)

oxoethyl}carboxamide (Compound of formula 14) (180 mg, 0.16 mmol) in EtoAC (5 ml) was added into 3M HCl-EtoAc (2 ml). Reaction was stirred for 30 minutes at room temperature. Take the TLC for the completion of reaction. Finally reaction was concentrated in vaccuo to yield [1-(2-amino-3-methylbutanoyl)pyrrolidin-2-yl]-N-{1-(methylethyl)-2-[2-(N-{1-(methylethyl)-2-oxo-2-(N-{3_oxo-3-[3-(trifluoromethyl)(1,2,4-triazolo[4,3-a]piperidin-6-yl)]-1-[(2,4,5-trifluorophenyl)methyl]propyl}carbamoyl)pyrrolidinyl]ethyl}carbamoyl)pyrrolidin-yl]-2-oxoethyl}carboxamide Hydrochloride (Compound of formula 15). (160 mg, 94.6%). Analytical Method to Estimate Release of Sitagliptin from Different DPP IV Derivatives Reagents and Solvents: Reagents, Solvents, Standards and Equipments:

Formula 14

Formula 15

To the stirred solution of (tert-butoxy)-N-{1-(methylethyl)-2-[2-(N-{1-(methylethyl)-2-[2-(N-{1-methylethyl)-2-oxo-2-[2-(N-{3-oxo-3-[3-(trifluoromethyl)(1,2,4-triazolo[4,3-a]piperidin-6-yl]-1-[2,4,5-trifluorophenyl)methyl]propyl}carbamoyl)pyrrolidinyl]ethyl}carbamoyl)pyrrolidinyl]-2-oxoethyl}carbamoyl)pyrrolidinyl]-2-

Trifluoro Acetic acid (AR grade)
Acetonitrile (HPLC grade)
Milli Q water
Sitagliptin Base as working standard DPP IV inhibitor
Shimadzu LC-2010 equipped with UV detector and Auto Sampler Diluent: Acetonitrile
Preparation of Buffer Transfer accurately measured 1000 mL Milli Q water in a beaker. Adjust pH 2.00±0.05 with Trifluoro acetic acid. Shake it gently and filter through 0.45μ membrane filter.

Preparation of Mobile Phase

Transfer 300 mL acetonitrile in 1000 mL volumetric flask and make the volume up to the mark with buffer pH 2.00±0.05

Standard Preparation

Exactly weigh about 20 mg Sitagliptin Base working standard in 10 mL volumetric flask. Add 5.0 mL diluent and sonicate it (if required) to dissolve the solids and make the volume up to the mark with diluent giving a standard solution having concentration 2000 ppm (Stock solution).

Above stock solution was further diluted to get different concentration solution varying from 0.025 μM to 100 μM. Linearity curve of peak area against concentration in μM was plotted for different concentration.

Sample Preparation

Extracted samples (after removing proteneous matter) were provide from different organs (Liver, Kidney and Pancreas) and serum samples which were directly injected on to HPLC system.

Chromatographic Conditions:

The liquid chromatography is equipped with variable wavelength UV detector, Auto sampler and Data processor
   Column: ypersil BDS C8, 4.6 mm×250 mm, 5μ
   Detector wavelength: 54 nm
   Flow Rate: 1.0 mL/min
   Injection volume: 20 μL
   Column Temperature: 60° C.

Procedure

Inject blank (diluent) and blank extraction samples, inject standard preparation of varying concentration from 0.025 μM to 100 μM and plot a graph of Area under curve against concentration in μM. Inject sample preparation and record the chromatogram. Disregard any peak due to blank and calculate concentration of Sitagliptin released from the extracted samples collected at different time intervals.

The retention time of Sitagliptine is about 5.0 to 6.0 minutes

Calculation

Calculate the concentration of released Sitagliptin from the extracted samples collected at different time intervals by extrapolating the area of Sitagliptin in samples against the standard linearity curve.

Figure 01:
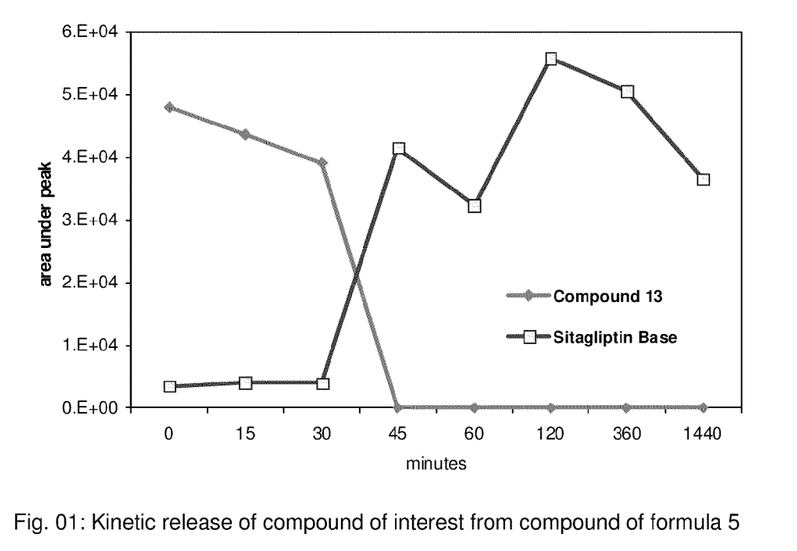
Figure 02:
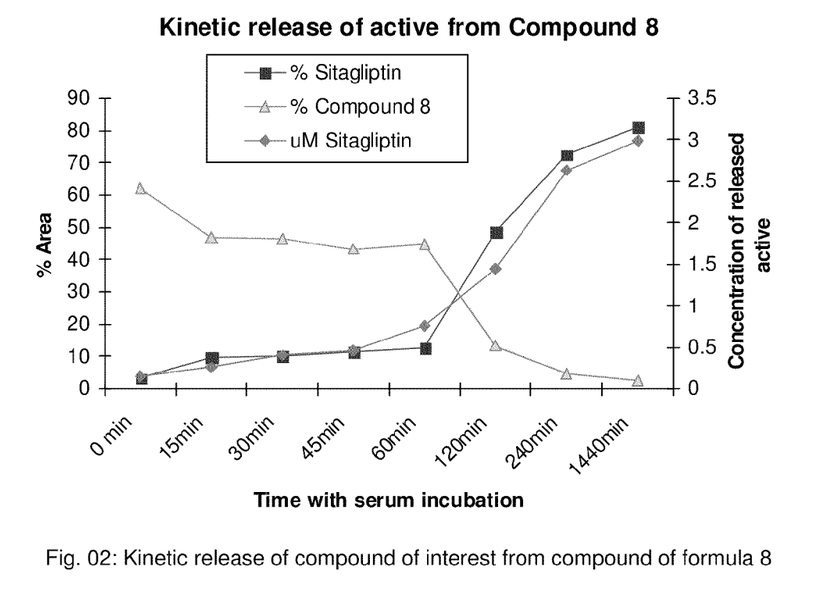
Figure 03:
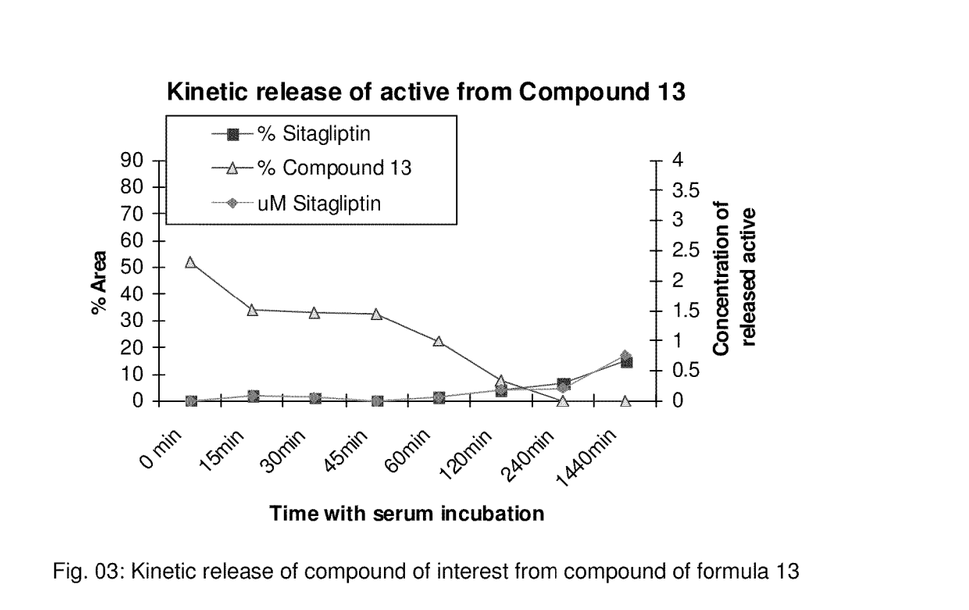
Figure 04:
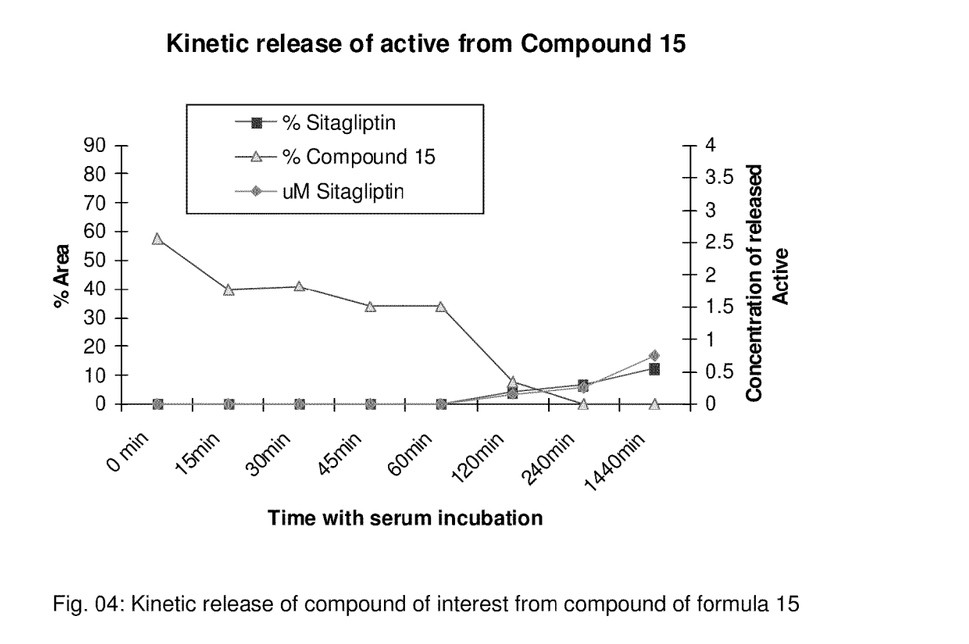

General Procedure for Screening:

Sitaglaptin dipeptide or Sitaglaptin base were Incubated with goat serum at 37° C. At time points: 0, 15, 30, 45 min, 1 hr, 2 hr, 6 hr & 24 hr samples were collected and solid phase extraction performed using Silica Extraction cartridges. Standards for both molecules were prepared in Acetonitrile+water (to check extraction efficacy). Samples were run on HPLC to evaluate the 'retention time' and 'area under the curve'. Retention time of the compound is used as parameter for identification of compounds. Area under the curve used to evaluate the quantity of the molecule present in reaction. The graphs are plotted for each compound as under.

The compounds disclosed in present invention are prepared by involving preferred process as described in known literature and useful to obtain the medicinally important active ingredient. The synthesized compounds are useful in a method of inhibiting dipeptidyl peptidase-IV enzyme in a patient such as a mammal in need of such inhibition comprising the administration of an effective amount of the compound. The present invention is directed to the use of the compounds disclosed herein as inhibitors of dipeptidyl peptidase-IV enzyme activity.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

The present invention is further directed to a method for the manufacture of a medicament for inhibiting DP-IV enzyme activity in humans and animals comprising combining a compound of the present invention with a pharmaceutical carrier or diluent.

While the invention has been described and illustrated with reference to certain particular embodiments thereof, those skilled in the art will appreciate that various adaptations, changes, modifications, substitutions, deletions, or additions of procedures for the preparation of the compounds as described in formula I and may modified departing from the spirit and scope of the invention.

We claim:

1. A compound having formula, wherein
A is a peptide consisting of 2 to 10 amino acids, wherein each amino acid is independently selected from glycine, alanine, valine, leucine, isoleucine, phenylalanine, methionine, tryptophan, glutamine, glutamic acid, serine, proline, cysteine, tyrosine, asparagine, aspartic acid, threonine or combinations thereof;
and B is a peptide bond;
or a pharmaceutically acceptable salt thereof.

2. The compound as claimed in claim 1, wherein the 2 to 10 amino acids are independently selected from glycine, alanine, valine, proline, phenylalanine, isoleucine, histidine or combinations thereof.

3. The compound as claimed in claim 1, wherein at least one of said 2 to 10 amino acids is proline or alanine.

4. A method for inhibiting dipeptidyl peptidase IV (DP-IV) enzyme in mammal comprising:
   administering a compound as claimed in claim 1 to a mammal.

* * * * *